United States Patent
Gould et al.

(10) Patent No.: US 6,673,054 B1
(45) Date of Patent: *Jan. 6, 2004

(54) BODY PROTECTION ARTICLE HAVING A GELATINOUS MATERIAL WITH A THERAPEUTIC ADDITIVE

(75) Inventors: Robert L. Gould, Teaneck, NJ (US); Ian Peter Whelan, Woodley (GB)

(73) Assignee: Silipos Inc., New York, NY (US)

( * ) Notice: Subject to any disclaimer, the term of this patent is extended or adjusted under 35 U.S.C. 154(b) by 412 days.

This patent is subject to a terminal disclaimer.

(21) Appl. No.: 09/654,581

(22) Filed: Sep. 1, 2000

Related U.S. Application Data

(63) Continuation-in-part of application No. 09/143,282, filed on Aug. 28, 1998, now Pat. No. 6,117,119.

(51) Int. Cl.[7] .............................................. A61M 35/00
(52) U.S. Cl. ...................... 604/292; 604/290; 604/293; 2/167; 602/21; 602/26; 602/27; 602/51
(58) Field of Search ................................ 604/289, 290, 604/292, 293; 2/167; 602/21, 26, 27, 48–51

(56) References Cited

U.S. PATENT DOCUMENTS

| | | | |
|---|---|---|---|
| 3,384,083 A | 5/1968 | Cozza et al. | |
| 3,640,741 A | 2/1972 | Etes | 106/170 |
| 3,827,999 A | 8/1974 | Crossland | 260/33.6 |
| 3,896,807 A | 7/1975 | Buchalter | 128/261 |
| 4,291,025 A | 9/1981 | Pellico | 424/180 |
| 4,369,284 A | 1/1983 | Chen | 524/476 |
| 4,456,642 A | 6/1984 | Burgdörfer et al. | 428/68 |
| 4,618,213 A | 10/1986 | Chen | 350/96.34 |
| 4,622,035 A | 11/1986 | Palmer et al. | 604/293 |
| 4,668,224 A | 5/1987 | Lentz et al. | 604/265 |
| 4,778,786 A | 10/1988 | Reever et al. | 514/54 |
| 4,842,931 A | 6/1989 | Zook | 428/354 |
| 4,853,978 A | 8/1989 | Stockum | 2/167 |
| 4,867,968 A | 9/1989 | Allen | 424/78 |
| 4,879,274 A | 11/1989 | Kamiya et al. | 514/12 |
| 5,098,421 A | 3/1992 | Zook | 604/367 |
| 5,153,254 A | 10/1992 | Chen | 524/505 |
| 5,158,555 A | * 10/1992 | Porzilli | 604/307 |
| 5,167,649 A | 12/1992 | Zook | 604/307 |
| 5,180,605 A | 1/1993 | Milner | 427/2 |
| 5,181,914 A | 1/1993 | Zook | 604/307 |
| 5,257,418 A | 11/1993 | Jaskiewicz | 2/20 |
| 5,262,468 A | 11/1993 | Chen | 524/476 |
| 5,328,449 A | 7/1994 | Andrews et al. | 602/42 |
| 5,330,452 A | 7/1994 | Zook | 604/307 |
| 5,334,646 A | 8/1994 | Chen | 524/474 |
| 5,336,209 A | * 8/1994 | Porzilli | 604/307 |
| 5,336,708 A | 8/1994 | Chen | 524/474 |

(List continued on next page.)

Primary Examiner—Weilun Lo
Assistant Examiner—Michael Bogart
(74) Attorney, Agent, or Firm—Darby & Darby

(57) ABSTRACT

The present invention is directed to a vitamin additive such as Vitamin A, $B_{12}$, C, D, E, incorporated into the thermoplastic material of a sock, glove or like body protection article. The thermoplastic material is preferably a block copolymer such as SEBS, SEPS and SEEPS copolymer. Additionally, the thermoplastic material can include natural oils such as grape seed oil, avocado oil, jojoba oil, canola oil, ceramides, aloe and olive oil.

32 Claims, 4 Drawing Sheets

U.S. PATENT DOCUMENTS

| | | | |
|---|---|---|---|
| 5,344,406 A | 9/1994 | Spooner | 604/179 |
| 5,357,636 A | 10/1994 | Dresdner, Jr. et al. | 2/161.7 |
| 5,480,646 A | 1/1996 | Vu | 424/443 |
| 5,489,437 A | 2/1996 | Marra | 424/443 |
| 5,497,789 A | 3/1996 | Zook | 128/893 |
| 5,508,334 A | 4/1996 | Chen | 524/474 |
| 5,549,924 A | 8/1996 | Shlenker et al. | 427/2.3 |
| 5,590,420 A | 1/1997 | Gunn | 2/69 |
| 5,596,770 A | 1/1997 | Kunesh | 2/239 |
| 5,632,045 A | 5/1997 | Chase et al. | 6/161.6 |
| 5,633,286 A | 5/1997 | Chen | 524/474 |
| 5,673,437 A | 10/1997 | Chase et al. | 2/167 |
| 5,679,399 A | 10/1997 | Shlenker et al. | 427/2.3 |
| 5,830,237 A | 11/1998 | Kania | 623/37 |
| 5,919,476 A * | 7/1999 | Fischer et al. | 424/443 |
| 5,965,276 A * | 10/1999 | Shlenker et al. | 428/492 |
| 6,143,946 A * | 11/2000 | Docter | 602/41 |
| 6,156,024 A * | 12/2000 | Schulte et al. | 604/385.28 |
| 6,335,388 B1 * | 1/2002 | Fotinos | 524/20 |

* cited by examiner

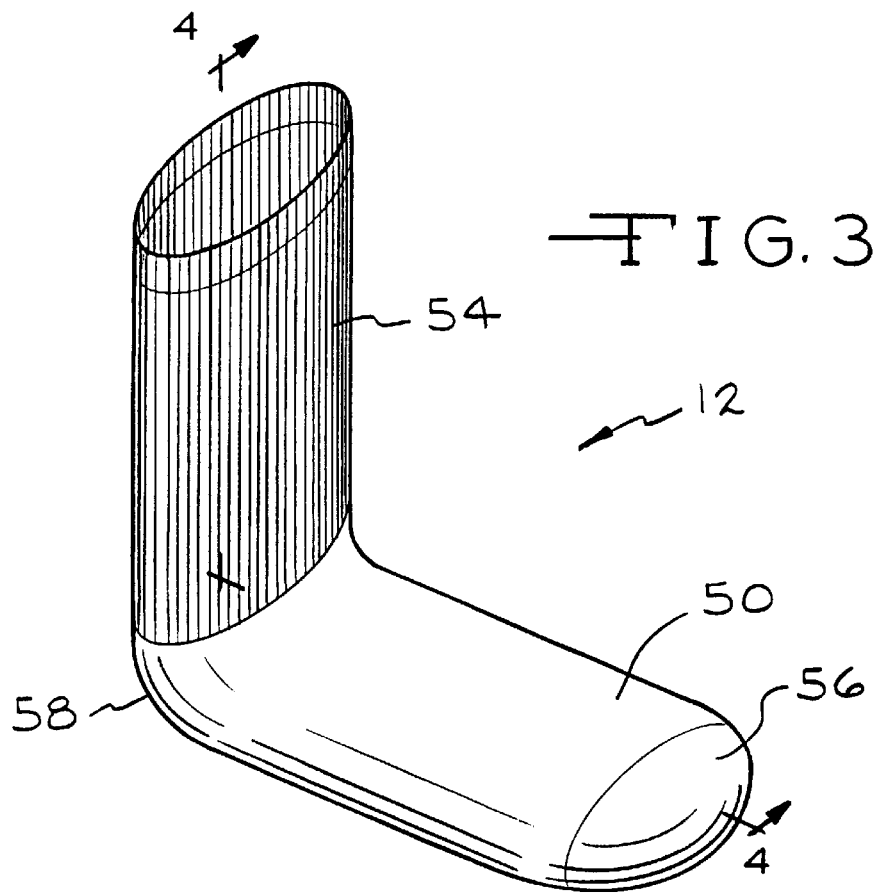
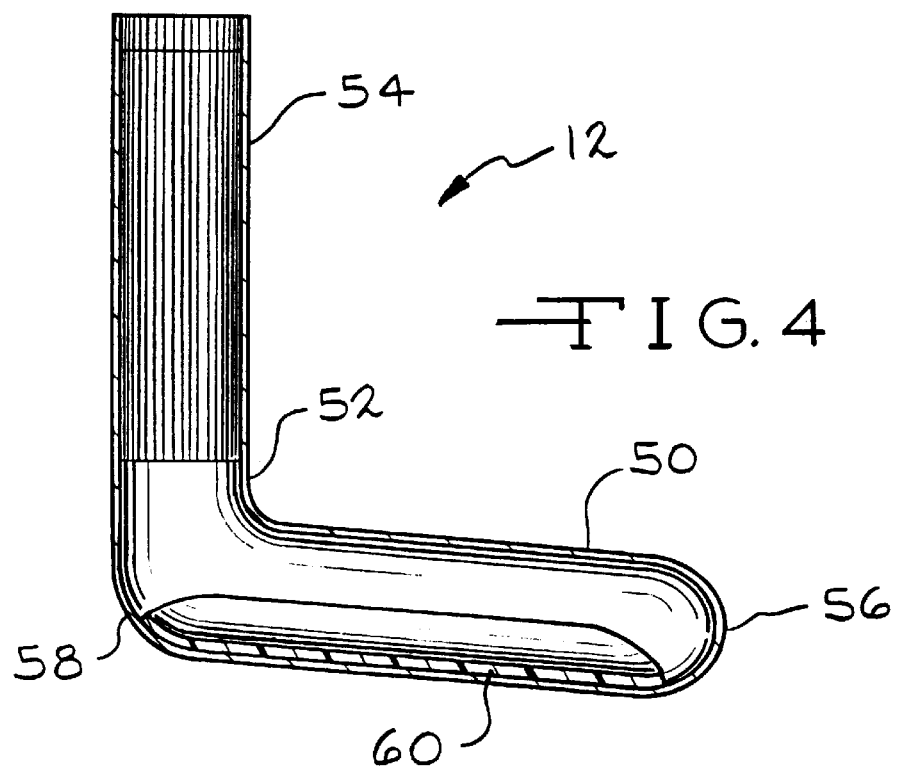

BODY PROTECTION ARTICLE HAVING A GELATINOUS MATERIAL WITH A THERAPEUTIC ADDITIVE

CROSS-REFERENCE TO RELATED APPLICATION

This application is a continuation-in-part application of Ser. No. 09/143,282, filed Aug. 28, 1998, now U.S. Pat. No. 6,117,119 to Gould.

BACKGROUND OF THE INVENTION

1. Field of the Invention

The present invention generally relates to a body protection article, and more particularly, to a body protection article comprising a gelatinous composition having an additive formulation for treating the protected skin. The body protection article can include a glove, socks, wrist band, brace for the knee, ankle, elbow and the like, or a shaped pad sized to cover any part of the body requiring delivery of a therapeutic active formulation to the skin. The gelatinous composition helps keep the skin moist while the therapeutically active formulation beneficially affects the well-being of the skin, such as skin sensitive to ultra violet light, burned skin, skin healing after a surgical procedure and the like.

2. Prior Art

It is known in the prior art to incorporate an additive into a gelatinous material formed into an article for wearing on the body to affect the well-being of the person. For example, U.S. Pat. Nos. 5,098,421; 5,167,649; 5,181,914; and 5,330,452, all to Zook describe various devices comprising a viscoelastic gel pad having pharmacologically active agents incorporated into the gel. U.S. Pat. No. 4,842,931 to Zook describes a pad made from a soft viscoelastic gel material containing a high percentage of plasticizing oil for equalizing pressure directed to corns, calluses, bunions and the like. It is also known to apply medication to the skin for the purpose of treating dermal afflictions and for delivering medicine to the body through the dermis. An example of such an externally applied medication is disclosed in U.S. Pat. No. 4,879,274 to Kamiya et al. which describes creams, ointments and the like comprising an α-monoglyceryl ether, a physiologically active material and an oily material. The physiologically active material comprises compounds such as drugs, growth hormones and the like including vitamins, for example, Vitamins A and $B_{12}$.

However, what is needed is a body protection article such as a glove, socks, shaped pad and the like that is comprised of a therapeutically active formulation-containing gelatinous composition that imparts beneficial properties to the skin protected by the article. Such benefits include, but are not limited to, reducing scar tissue from burned skin and skin healing from a surgical procedure by maintaining the skin in a moist and lubricated state, treatment of skin blemishes and providing gentle compression to cushion and help absorb shock forces directed to the body.

SUMMARY OF THE INVENTION

The body protection article according to the present invention comprises a thermoplastic, gelatinous elastomeric composition containing a therapeutically active formulation as an additive incorporated therein. When the gelatinous composition is intimately combined with a substrate such as a cloth material, paper or a polymeric film provided as a piece of clothing or a shaped pad sized to cover a particular part of the body, the therapeutically active formulation is released from the gel to affect the well-being of the person wearing the article. The gelatinous composition is preferable a block copolymer of the general configuration poly(styrene-ethylene-butylene-styrene), poly(styrene-ethylene-propylene-styrene) and poly(styrene-ethylene-ethylene-propylene-styrene) combined within a plasticizing oil. Preferred therapeutically active formulation includes vitamin and/or natural oil additives.

These and other aspects of the present invention will become more apparent to those skilled in the art by reference to the following description and to the appended drawings.

BRIEF DESCRIPTION OF THE INVENTION

FIG. 3 is an elevational view of a sock according to the present invention.

FIG. 4 is a cross-sectional view along line 4—4 of FIG. 3.

DETAILED DESCRIPTION OF THE INVENTION

Figure 1:
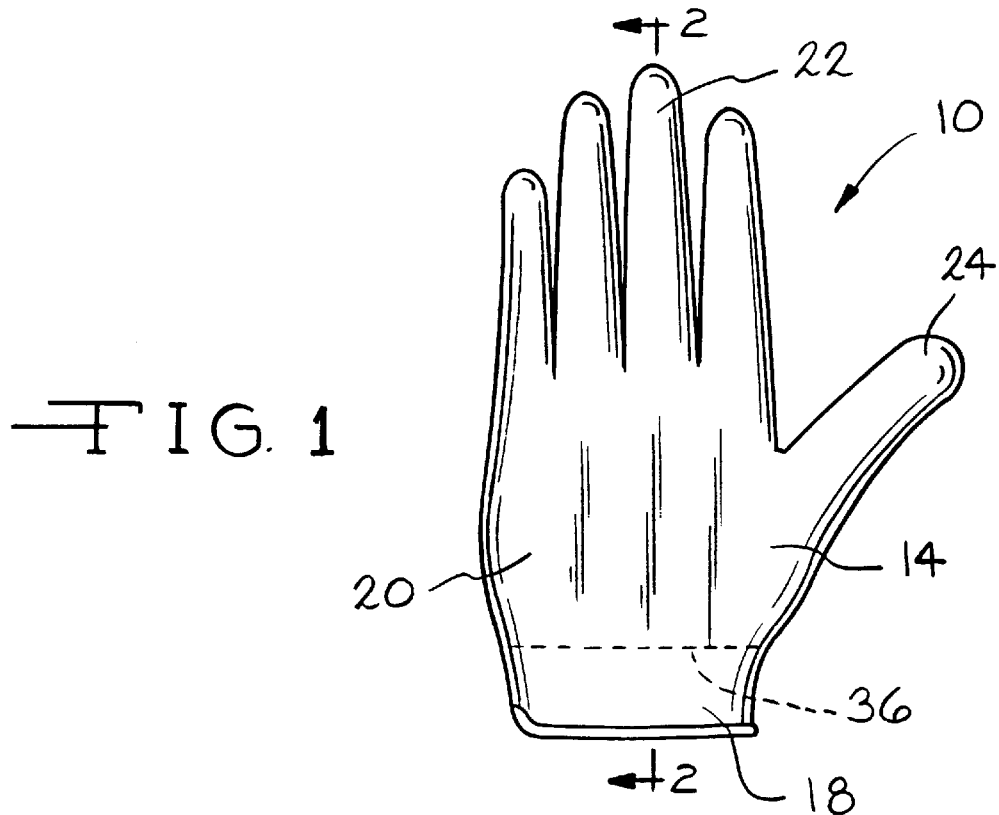
FIG. 1 is an elevational view of a glove according to the present invention.
Figure 2:
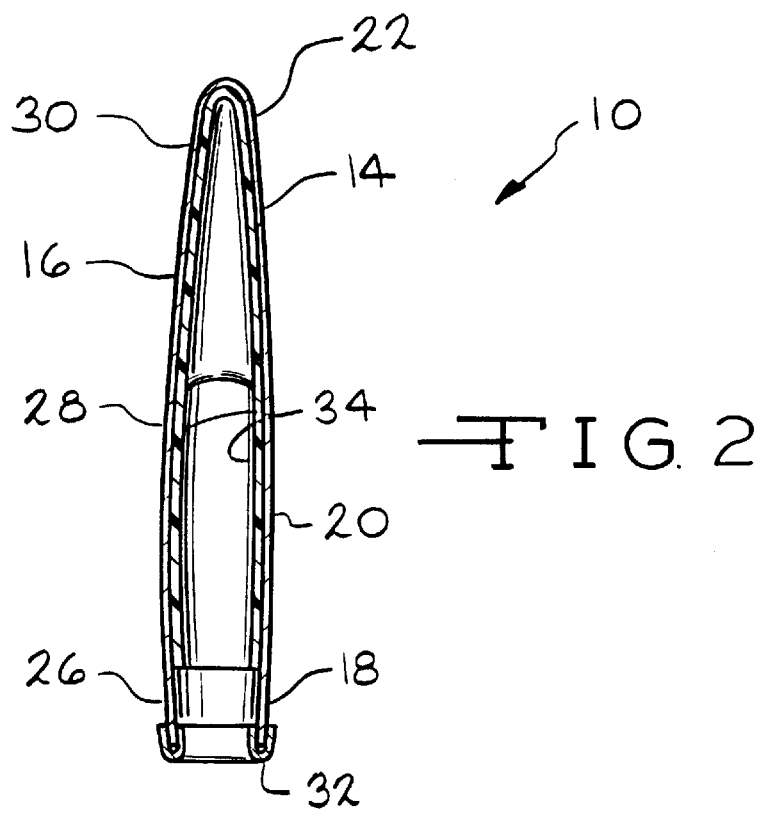
FIG. 2 is a cross-sectional view along line 2—2 of FIG. 1.

Turning now to the drawings, FIGS. 1 to 4 show various embodiments of body protection articles constructed according to the principles of the present invention. FIGS. 1 and 2 show a glove 10 and FIGS. 3 and 4 illustrate a sock 12. However, those skilled in the art will readily appreciate that the glove 10 and sock 12 shown are only exemplary, and many different articles worn on the body are useful for imparting a therapeutically active formulation to the covered skin delivered from a gelatinous elastomeric composition according to the present invention. In a broader sense, however, a body protective article is provided in any shape and size required to cover a particular body part including shaped pads for use by women, men and children of all ages and sizes.

As shown in FIGS. 1 and 2, the glove 10 is comprised of a palm piece 14 and a backhand piece 16, each a mirror image of the other. The palm piece 14 includes a wrist portion 18 extending across a palm portion. 20 to four finger extensions 22 and a thumb extension 24. The back piece 16 of the glove similarly has a wrist portion 26 extending across a backhand portion 28 to form finger extensions 30 and a thumb extension (not shown). The palm piece 14 and the backhand piece 16 are joined together at their peripheral edges, such as by sewing, except at the respective wrist portions 18 and 26 providing an opening for putting a hand in the glove. A wrist piece 32 is folded over onto both sides of the palm piece 14 and the backhand piece 16 and sewn thereto surrounding the glove opening to prevent fraying and to add integrity for pulling the glove 10 onto a hand and for removing it therefrom.

The palm piece 14 and the backhand piece 16 are made from a cloth material having a gelatinous elastomeric composition 34 intimately bonded thereto. The gelatinous composition 34 extends from a location spaced from the wrist piece 32, as shown by the dashed line 36, to the ends of the fingers 22, 30 and the thumb 24. Preferably the inner surface of the gelatinous composition closest to the human hand wearing the glove 10 directly contacts the skin.

The cloth material can be a knitted fabric constructed of both synthetic and natural yarns. Suitable synthetic materials includes yarns such as polyester, polyamide such as rayon, nylon, polyolefin, acrylic and like fibers while suitable natural fibers include cotton, cambric, wool, cashmere, jute and others.

FIGS. 3 and 4 show a sock 12 according to another embodiment of the present invention. The sock 12 is comprised of foot portion 50 leading to an ankle portion 52 extending to a lower leg portion 54. The sock 12 can be made having a generally tubular construction closed at one end by a toe portion 56 and seamed to provide a heel recess 58. In a similar manner as the glove 10, the sock 12 is made from a knitted cloth having a gelatinous elastomeric composition 60 intimately bonded thereto. The cloth and gelatinous composition of the sock 14 are selected from materials similar to those used to construct the respective palm and backhand pieces 14, 16 and the gelatinous composition 34 of the glove 10.

The gelatinous material preferably directly contacts the skin in a similar manner as shown and described with respect to the glove 10 to medicate the protected skin by means of a therapeutically active formulation as an additive incorporated therein. As shown in the cross-sectional view of FIG. 4, the gelatinous composition 60 extends from the toe portion 56 to the heel 58 and has a width sufficient to cover the bottom of the foot.

Suitable gelatinous compositions are prepared by melt blending an admixture comprising: about 1 part by weight of a high viscosity triblock copolymer of the general configurations poly(styrene-ethylene-butylene-styrene) (SEBS), poly(styrene-ethylene-propylene-styrene) (SEPS) or poly (styrene-ethylene-ethylene-propylene-styrene) (SEEPS), and from about 2 to about 15 parts by weight of a plasticizing oil. The block copolymer materials are commercially available from various sources including Shell under the Kraton designation, Kuraray Co, Ltd.

It will be understood that the block copolymer may comprise more complicated structures of either linear or branched configurations and may contain any desired number of polymer blocks as long as each of them has the identify and block molecular weights considered here. The block molecular weights employed for the present purpose are 5,000 to 75,000 average molecular weight in the monoalkylarene polymer blocks (preferably 8,000 to 65,000) and 25,000 to 250,000 average molecular weight for the hydrogenated blocks of conjugated dienes (preferably 35,000 to 110,000).

The block copolymers are characterized as having a Brookfield viscosity of a 20 weight percent solids solution of the block copolymer in toluene at 25° C. of about 1,800 cps and higher. Less typically, the Brookfield viscosity values of the block copolymer can range from about 1,800 cps to about 30,000 cps or higher.

Particularly preferred moderate to high viscosity SEPS and SEEPS block copolymers include Kuraray's 2006 and 4055 designations, which exhibit solution viscosities at 10 weight %, 30° C. of about 7.1 and 59, respectively, and styrene contents, by weight, of about 35% and 30%, respectively. For a more detailed description of block polymers that are useful with the present invention, reference is made to U.S. Pat. No. 3,827,999 to Crossland, the disclosure of which is incorporated herein by reference. Recent reviews of triblock copolymers are found in the "ENCYCLOPEDIA OF POLYMER SCIENCE AND ENGINEERING", Volumes. 2 and 5, 1987–1988; "Thermoplastic Elastomers", MODERN PLASTIC ENCYCLOPEDIA, 1989; and Walker, B. M., Ed., et al., HANDBOOK OF THERMOPLASTIC ELASTOMERS, Van Nostrand Reinhold Co., 2nd Edition, 1988. These publications are incorporated herein by reference.

The gelatinous block materials are mixed with a plasticizing oil to provide compositions that can be softened or melted at elevated temperatures but which regain elastomeric properties at ambient temperatures. Plasticizing oils particularly preferred for use in practicing the present invention are well known in the art. They include rubber processing oils such as paraffinic and naphthionic petroleum oils, highly refined aromatic-free paraffinic and naphthionic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Examples of representative commercially available plasticizing oils include Amoco® polybutenes, hydrogenated polybutenes and polybutenes with epoxide functionality at one end of the polybutene polymer and ARCO Prime, Duraprime and Tufflo oils. Other white mineral oils include: Bayol, Bernol, American, Blandol, Drakeol, Ervol, Gloria, Kaydol, Litetek, Lyondell's Duraprime series, Marcol, Parol, Peneteck, Primol, Protol, Sonrex, and the like. Generally, plasticizing oils with average molecular weights less than about 200 and greater than about 700 may also be used.

According to the present invention, an effective amount of a therapeutically active formulation comprising a vitamin additive is incorporated into the gelatinous/plasticizing oil mixture. The vitamin additive is selected from the group of Vitamin A, $B_{12}$, C, D, E, and mixtures thereof. Preferably, the vitamin additive is present in the therapeutically active formulation at a concentration of, by weight percent, about 1% to about 10%. The present invention further contemplates that any one of a number of medical grade natural oils can be incorporated into the therapeutically active formulation which is subsequently added to the gelatinous/plasticizing oil mixture. Suitable medical grade natural oils include grape seed oil, avocado oil, jojoba oil, canola oil, ceramides, olive oil, aloe, and mixtures thereof. Preferably, the natural oil is present in the gelatinous elastomeric composition at a concentration of, by weight percent, about 5% to about 35%. After the therapeutically active formulation has been provided, it is admixed with the gelatinous material/plasticizing oil in a range of, by weight, about 5% to about 50%. In some formulations, the natural oils can be used in lieu of the plasticizing oil to provide the resulting composition having the desired viscosity. In that case, the therapeutically active formulation is added to the gelatinous material, by weight, up to about 80%.

The gelatinous elastomeric composition can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

The gelatinous elastomeric composition of the present invention may be made non-adhering, non-sticking, non-tacky by incorporating therein a suitable amount of one or more of a metal stearate selected from calcium stearate, magnesium stearate, zinc stearate, aluminum stearate, and the like, and a suitable amount of one or more of a fatty amide selected from oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, and the like, or a suitable wax selected from polyethylene, polypropylene, microcrystalline, carnauba, paraffin, montan, candelilla, beeswax, ozokerite, ceresine, and the like.

The gelatinous elastomeric compositions of the present invention are prepared by blending together the block copolymer, plasticizing oil and the therapeutically active formulation comprising the vitamin additive and preferably the natural oil components as desired at about 23° C. to about 100° C., forming a paste like mixture and further heating the mixture to about 150° C. to about 250° C. until a homogeneous molten blend is obtained. Lower and higher temperatures can also be utilized depending on the viscosity of the oils and amount of the block copolymer used. These components blend easily in the melt and a heated vessel equipped with a stirrer is all that is required.

An exemplary formulation for the therapeutically active component before incorporation into the gelatinous composition is as follows:

| INGREDIENTS | WEIGHT % |
|---|---|
| Olive Oil | 25.00 |
| Canola Oil | 25.00 |
| Jojoba Oil Lite | 25.00 |
| Grape Seed Oil | 12.00 |
| N-stearyl phytosthingosine SoyBean Extract | 10.00 |
| Vitamin E Acetate | 2.00 |
| Fragrance | 0.80 |
| Di-tert-butyl-t-cresol (Food Grade) | 0.20 |

Thus, the present invention body protection articles are formed from a molten blend of the gelatinous elastomeric material, plasticizing oil and the therapeutically active formulation comprising the vitamin additive, and optionally at least one of the enumerated natural oils intimately bonded to a cloth, fabric, paper or a polymeric film substrate by blending, melting, dipping, casting, injection molding, extruding and other conventional methods. For example, a preselected rigidity of a molten gelatinous elastomer composition is cast directly onto a cloth material to form the body protection article such as glove 10 and sock 12. The gelatinous elastomer composition can also be die cast, cut to size and heat bonded to the substrate. Likewise, a substrate such as of a cloth, paper, or a polymeric film material can be dipped into a preselected rigidity of a molten gelatinous elastomer composition and re-dipped into the same or different composition of a different rigidity. The shaped composite article of the invention can be conventionally covered with protective skins of elastomeric film, paper, cloth, fabric or combinations thereof, as needed.

Figure 5:
FIGS. 5 and 6 are photographs showing a surgically repaired hand before and after contact with a gelatinous composition having an additive for treating the protected area.
Figure 6:

Such a gelatinous elastomeric composition contacted to a surgical incision on a hand by means of a glove according to the present invention results in reduced scarring to the extent that after treatment, the area of an incision is nearly of the same texture and elasticity as that of undamaged skin. FIGS. 5 and 6 are respective photographs showing a hand before contact with a gelatinous composition according to the present invention comprising a SEEPS block copolymer, plasticizing oil and the exemplary therapeutically active formulation set forth above, and about 42 days after contact with the composition of the present invention by means of glove 10. It is believed that the gelatinous elastomeric material serves as an occlusive blanket for "driving" the vitamin and natural oil additives into the skin. In that manner the medical grade natural oil slowly dissipates from the gelatinous material onto the skin or scar to moisturize and lubricate the affected area. This is particularly advantageous for reducing the discoloration and thickness of both new and old keloid and hypertrophic scars in addition to improving the elasticity of the skin. The present invention can also be, practiced in the form of shaped pads for treating facial conditions such as blemishes, liver spots, wrinkles and the like.

Many other therapeutic agents can be incorporated into the gelatinous elastomeric compositions of the present invention. For example, antifungal agents (fungal agents) such as ciclopirox, chloroxylenol, undecylenic acid, tolnaftate, miconizole, clotrizole, griseofulvin, clotrimazole, butenafine, terbinafine, fluconazole, itraconazole, chlorbutanol, zinc undecanote, undecanoic acid, benzyl peroxide, potassium hydroxyquinalone, aluminium chloride hexahydrate, saclicyclic acid, aciclovir and ketoconozole may be incorporated therein. Antibiotic agents such as mupirocin, erythromycin, gentimycin, neomycin, polymyxin, bacitracin, tetracyclines, and the like may also be incorporated into the gelatinous composition.

Antiseptic and antibacterial agents such as iodine, povidone-iodine, benzalkonium chloride, benzoic acid, chlorhexidine, nitrofurazone, benzoyl peroxide, hexachlorophene, phenol, resorcinol, chlorhexideine gluconate, hexetidine, chlorbutanol, dibromopropamidine isothionate, triclosan, chloroxylenol, cetrimide, benzocaine, methyl salicylate, hydrogen peroxide, hexachloropentane, potassium hydroyquinolone, chlorocresol, lidocaine, framycetin sulphate, muprocin, neomycin sulphate, colistin sulphate, polymoxin sulphate, silver sulfadiazine, chlorotetracycline, fusidic acid, metronidazole, tetracycline, and cetylpyridinium chloride likewise could be incorporated into the present invention.

Furthermore, anti-inflammatories such as hydrocortisone, prednisone, triamcilolone, betamethasone and the like may be incorporated into the gelatinous composition.

Still further, local anesthetics such as benzocaine, lidocaine, procaine, bupivicaine, a eutectic mixture of prilocaine and lignocaine, phenol, diphenhydramine, and the like may also be incorporated into the gelatinous composition.

Anti-allergy agents may be included into the gelatinous elastomeric compositions, and they include benzocaine, diphenhydramine, mepyramine, hydrocortisone, chlorbutanol, lignocaine, crotamiton, triclosan, aluminium sulphate, and antazoline.

Analgesics may be included in the gelatinous elastomeric compositions, and they include ibuprofen, ibuprofen lysinate, ibuprofen sodium, aloxiprin, dihydrocodiene, codiene phosphate, doxylamine succinate, carbenoxelone sodium, lidocaine, benzocaine, chlorocresol, cetalkonium chloride, salicylates, capsicum oleate, nicotinates, ketoprofen, naproxen, diclofenac, terpineol, piroxicam, and felbinac.

Topical corticosteroids are also useful additives in the gelatinous elasomeric composition, and they include hydrocortisone, aclometasone, beclometasone, betamethasone, clobetasol, clobetasone, desoxitnethasone, diflucortolone, fluocinolone, and fluocinonide.

Compounds such as gamolenic acid, lithium succinate, calcipotriol, tacalcitol, tazarotene, and dithranolsalicylic acid are useful for preventing eczema and psoriasis when incorporated into the present gelatinous elastomeric composition.

Additional agents that could be incorporated include penetration enhancers such as dimethyl sulfoxide or octolyphenylpolyethelene glycol, keratolytic agents such as salicylic acid, enzymes such as proteases and nucleases, hormones such as insulin, vesicants such as cantharadin, caustics such as podophyllin, and a myriad of additional pharmacologically active substances.

It is appreciated that various modifications to the inventive concepts described herein may be apparent to those of ordinary skill in the art without departing from the spirit and scope of the present invention as defined by the appended claims.

What is claimed is:

1. A body protection article, which comprises:
   (a) a substrate;
   (b) a gelatinous material comprising a block polymer intimately bounded to the substrate;
   (c) a first therapeutically active agent incorporated into the gelatinous material, wherein the first therapeutically active agent is selected from the groups consisting of Vitamins A, $B_{12}$, C, D, E, and mixtures thereof; and
   (d) a second therapeutically active agent incorporated into the gelatinous material, wherein the second therapeutically active agent is a natural oil selected from the group consisting of grape seed oil, avocado oil, jojoba oil, canola oil, ceramides, aloe, olive oil, and mixtures thereof.

2. The body protection article of claim 1 wherein the gelatinous material is selected from the group consisting of SEBS, SEPS, SEEPS, and mixtures thereof.

3. The body protection article of claim 1 wherein the substrate is selected from the group consisting of cloth, paper, a polymeric film, and mixtures thereof.

4. The body protection article of claim 1 wherein the substrate is a synthetic material selected from the group consisting of polyester, polyamide, polyolefin, acrylic, and mixtures thereof.

5. The body protection article of claim 1 wherein the substrate is a natural material selected from the group consisting of cotton, cambric, wool, cashmere, rayon, jute, and mixture thereof.

6. The body protection article of claim 1 selected from the group consisting of a glove, sock, brace for a knee, ankle and elbow, and a shaped pad.

7. The body protection article of claim 1 wherein the gelatinous material further includes a third agent selected from the group consisting of an antifugal agent, an antibiotic agent, an anesthetic, a penetration enhancer, a keratotytic agent, an enzyme, a hormone, a caustic agent, an anti-allergy agent, an analgesic agent, a topical corticosteroid, an anti-eczema agent, an anti-psoriasis agent, and mixtures thereof.

8. The body protection article of claim 1 wherein the gelatinous material further includes an antifungal agent selected from the group consisting of ciclopirox, chloroxylenol, undecylenic acid, tolnaftate, miconizole, clotrizole, griseofulvin, clotrimazole, butenafine, terbinafine, fluconazole, itraconazole, chlorbutanol, zinc undecanote, undecanoic acid, benzyl peroxide, potassium hydroxyquinalone, aluminum chloride hexahydrate, saclicylic acid, acyclovir, ketoconozole, and mixtures thereof.

9. The body protection article of claim 1 wherein the gelatinous material further includes an antibiotic agent selected from the group consisting of mupirocin, erythromycin, gentimycin, neomycin, polymyxin, bacitracin, tetracyclines, and mixtures thereof.

10. The body protection article of claim 1 wherein the gelatinous material further includes an antiseptic agent selected from the group consisting of iodine, povidone-iodine, benzalkonium chloride, benzoic acid, chlorhexidine, nitrofurazone, benzoyl peroxide, hexachlorophene, phenol, resorcinol, chlorhexideine gluconate, hexetidine, chlorbutanol, dibromopropamidine isothionate, triclosan, chloroxylenol, cetrimide, benzocaine, methyl salicylate, hydrogen peroxide, hexachloropentane, potassium hydroxyquinalone, chlorocresol, lidocaine, framycetin sulphate, muprocin, neomycin sulphate, colistin sulphate, polymoxin sulphate, silver sulfadiazine, chlorotetracycline, fusidic acid, metronidazole, tetracycline, cetylpyridinium chloride, and mixtures thereof.

11. The body protection article of claim 1 wherein the gelatinous material further includes an anti-inflammatory agent selected from the group consisting of hydrocortisone, prednisone, triamcilolone, betamethasone, and mixtures thereof.

12. The body protection article of claim 1 wherein the gelatinous material further includes an anesthetic agent selected from the group consisting of benzocaine, lidocaine, procaine, bupivicaine, a eutectic mixture of prilocaine and lignocaine, phenol, diphenhydramine, and mixtures thereof.

13. The body protection article of claim 1 wherein the gelatinous material further includes an anti-allergy agent selected from the group consisting of benzocaine, diphenhydramine, mepyramine, hydrocortisone, chlorbutanol, lignocaine, crotamiton, triclosan, aluminum sulphate, antazoline, and mixtures thereof.

14. The body protection article of claim 1 wherein the gelatinous material further includes an analgesic agent selected from the group consisting of ibuprofen, ibuprofen lysinate, ibuprofen sodium, aloxiprin, dihydrocodeine, codeine phosphate, doxylamine succinate, carbenoxelone sodium, lidocaine, benzocaine, chlorocresol, cetalkonium chloride, salicylates, capsicum oleate, nicotinates, ketoprofen, naproxen, diclofenac, terpineol, piroxicam, felbinac, and mixtures thereof.

15. The body protection article of claim 1 wherein the gelatinous material further includes a topical corticosteroid selected from the group consisting of hydrocortisone, aclometasone, beclometasone, betamethasone, clobetasol, clobetasone, desoxitnethasone, diflucortolone, fluocinolone, fluocinonide, and mixtures thereof.

16. The body protection article of claim 1 wherein the gelatinous material further includes an anti-eczema agent or an anti-psoriasis agent selected from the group consisting of gamolenic acid, lithium succinate, calcipotriol, tacalciol, tazarotene, dithranolsalicylic acid, and mixture thereof.

17. A method for providing a body protection article, comprising the steps of:
   (a) providing a substrate;
   (b) incorporating a first therapeutically active agent into a gelatinous material comprising a block polymer, wherein the first therapeutically active agent is selected from the group consisting of Vitamins A, $B_{12}$, C, D, E, and mixtures thereof;
   (c) incorporating a second therapeutically active agent into the gelatinous material, wherein the second therapeutically active agent is a natural oil selected from the group consisting of grape seed oil, avocado oil, jojoba oil, canola oil, ceramides, aloe, olive oil, and mixtures thereof; and
   (d) bonding the gelatinous material to the substrate.

18. The method of claim 17 including selecting the gelatinous material from the group consisting of SEBS, SEPS and SEEPS, and mixtures thereof.

19. The method of claim 17 including selecting the substrate from the group consisting of cloth, paper, a polymeric film, and mixtures thereof.

20. The method of claim 17 including providing the body protection device as one selected from the group consisting of a glove, sock, brace for a knee, ankle and elbow, and a shaped pad.

21. The method of claim 17 including providing the substrate as a cloth of natural materials selected from the group consisting of cotton, cambric, wool, cashmere, rayon, jute, and mixtures thereof.

22. The method of claim 17 wherein the gelatinous material is mixed with a plasticizing oil in a ratio of about 1:2 to 1:15.

23. The method of claim 17 wherein the gelatinous material is mixed with a plasticizing oil, the first therapeutically active agent and the second therapeutically active agent at a temperature of about 23° C. to about 250° C.

24. The method of claim 17 wherein the gelatinous material is mixed with a plasticizing oil, the first therapeutically active agent, and the second therapeutically active agent at a first temperature range of about 23° C. to about 100° C. to form a paste like mixture, followed by a further heating at a second temperature range of about 150° C. to about 250° C.

25. The method of claim 17 wherein the gelatinous material is rendered non-adhering, non-sticking and non-tacky by incorporating therein a metal stearate, and at least one of a fatty amide and a wax.

26. The body protection article of claim 4 wherein the synthetic material is polyamide.

27. The body protection article of claim 8 wherein the gelatinous material is a block co-polymer selected from the group consisting of SEBS, SEPS, and SEEPS, and mixtures thereof.

28. The body protection article of claim 8 wherein the substrate is a member selected from the group consisting of cloth, paper, a polymeric film and mixtures thereof.

29. The body protection article of claim 8 wherein body protection device is selected from the group consisting of a glove, sock, brace for a knee, ankle and elbow, and a shaped pad.

30. The body protection article of claim 8 wherein the substrate is a cloth of natural materials selected from the group consisting of cotton, cambric, wool, cashmere, rayon, jute, and mixtures thereof.

31. The body protection article of claim 8 wherein the gelatinous material is mixed with a plasticizing oil in a ratio of about 1:2 to 1:15.

32. The body protection article of claim 8 wherein the gelatinous material includes a metal stearate, and at least one of a fatty amide and a wax.

* * * * *

UNITED STATES PATENT AND TRADEMARK OFFICE
CERTIFICATE OF CORRECTION

PATENT NO. : 6,673,054 B1
DATED : January 6, 2004
INVENTOR(S) : Robert L. Gould et al.

It is certified that error appears in the above-identified patent and that said Letters Patent is hereby corrected as shown below:

<u>Title page,</u>
Item [75], Inventors, delete "Robert L. Gould, Teaneck, NJ" and substitute
-- Robert L. Gould, New York, NY --.

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,673,054 B1
DATED : January 6, 2004
INVENTOR(S) : Robert L. Gould et al.

It is certified that error appears in the above-identified patent and that said Letters Patent is hereby corrected as shown below:

Column 7,
Line 45, step (b) "bounded" should be -- bounded --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,673,054 B1
DATED : January 6, 2004
INVENTOR(S) : Robert L. Gould et al.

It is certified that error appears in the above-identified patent and that said Letters Patent is hereby corrected as shown below:

Column 7,
Line 17, step (b) "bounded" should be -- bonded --.

This certificate supersedes Certificate of Correction issued June 1, 2004.

Signed and Sealed this

Twenty-ninth Day of March, 2005

JON W. DUDAS
*Director of the United States Patent and Trademark Office*